United States Patent
Hung

(10) Patent No.: US 6,229,611 B1
(45) Date of Patent: May 8, 2001

(54) METHOD OF DETECTING A TRANSPARENT QUARTZ WAFER IN A SEMICONDUCTOR EQUIPMENT

(75) Inventor: Tz-Ian Hung, Hsin-Ying (TW)

(73) Assignee: United Microelectronics Corp.

( * ) Notice: Subject to any disclaimer, the term of this patent is extended or adjusted under 35 U.S.C. 154(b) by 0 days.

(21) Appl. No.: 09/399,090

(22) Filed: Sep. 20, 1999

(51) Int. Cl.[7] .................................................. G01N 21/00
(52) U.S. Cl. ........................................................... 356/432
(58) Field of Search .................................... 356/432, 372, 356/373, 375, 399, 400; 250/559.01, 559.29, 559.36, 559.4

(56) References Cited

U.S. PATENT DOCUMENTS

| | | | |
|---|---|---|---|
| 4,643,950 | * | 2/1987 | Ogura et al. ........................... 428/446 |
| 5,340,261 | * | 8/1994 | Oosawa et al. ........................ 414/217 |
| 5,354,995 | * | 10/1994 | Endo et al. ............................ 250/561 |
| 5,358,808 | * | 10/1994 | Nitayama et al. ......................... 430/5 |
| 5,798,532 | * | 8/1998 | Linehan ............................ 250/559.22 |
| 5,926,701 | * | 7/1999 | Li ......................................... 438/158 |
| 5,949,091 | * | 9/1999 | Yamaguchi ............................. 257/64 |
| 5,999,268 | * | 12/1999 | Yonezawa et al. ................... 356/399 |

\* cited by examiner

*Primary Examiner*—Frank G. Font
*Assistant Examiner*—Michael P. Stafira
(74) *Attorney, Agent, or Firm*—Winston Hsu

(57) ABSTRACT

This invention provides a method of detecting a transparent quartz wafer in a semiconductor equipment used to perform a specific process over a silicon wafer and comprising a light source and a optic sensor. When the silicon wafer is moved into the equipment, it will block the light and the equipment is switched on to perform the specific process. The method is forming a thin film layer at the bottom side of the quartz wafer over which thin film layer can absorb at least portion of light transmitted from the light source. When the quartz wafer is moved into the equipment, the thin film layer can absorb portion light so as to make the optic sensor detect the quartz wafer and then the equipment will be switched on to perform the specific process.

5 Claims, 1 Drawing Sheet

METHOD OF DETECTING A TRANSPARENT QUARTZ WAFER IN A SEMICONDUCTOR EQUIPMENT

BACKGROUND OF THE INVENTION

1. Field of the Invention

The present invention relates to a method of detecting a transparent quartz wafer, and more particularly, to a method of detecting a transparent quartz wafer in a semiconductor equipment.

2. Description of the Prior Art

The quartz wafer is widely used as the substrate of the large-scaled thin film transistor liquid crystal display(TFT-LCD). As the demand of the liquid crystal display becomes higher, the manufacturing process of the quartz wafer becomes more important. Because the quartz wafers is almost completely transparent, there are many restrictions in performing the process of the quartz wafer by using the semiconductor equipment originally used for the process of the silicon wafer. Since the semiconductor equipment for processing the silicon wafer is highly developed at present, how to utilize the semiconductor equipment in processing the quartz wafer to benefit from the advances becomes an important issue for the semiconductor research.

Please refer to FIG. 1. FIG. 1 is a schematic diagram of a method of detecting a silicon wafer 12 in a semiconductor equipment 10 according to the prior art. The semiconductor equipment 10 is used to perform a specific manufacturing process over semiconductor silicon wafers and comprising a light source 14 and a optic sensor 16 for detecting the light transmitted from the light source 14. The light source 14 may be an infrared or a red light source. The semiconductor silicon wafer 12 is moved into the semiconductor equipment 10 along a predetermined direction 18. Because the semiconductor silicon wafer 12 itself does not allow lights to penetrate through, when the semiconductor silicon wafer 12 is moved to a predetermined position in the semiconductor equipment 10, it will block the light 20 transmitted from the light source 14 to the optic sensor 16 and then the semiconductor equipment 10 will be switched on to perform the specific manufacturing process.

The quartz wafer is a kind of crystal material which is almost completely transparent. If performing the specific manufacturing process over the quartz wafer by using the semiconductor equipment 10 originally developed for processing the semiconductor silicon wafers, the process over the quartz wafer can not be properly controlled. Because the light 20 transmitted form the light source 14 will almost completely pass through the quartz wafer into the optic sensor 16, and the semiconductor equipment 10 cannot detect the existence of the quartz wafer as it is moved to a predetermined position, and hence it is difficult to control the timing for switching on the specific manufacturing process.

Because the common semiconductor equipment used for processing the silicon wafers cannot be used for processing the quartz wafers, the optic sensor in the semiconductor equipment need to be replaced by other sensor in order to process the quartz wafers. Otherwise, it is necessary to purchase the whole machine specifically designed for processing quartz wafers. However, many complex machines are involved in completing the series of manufacturing processes of the TFT-LCD, it will be very time-consuming and costly to replace each of the sensors in the equipment or to change the machines.

SUMMARY OF THE INVENTION

It is therefore a primary objective of the present invention to provide a method of detecting a transparent quartz wafer in a semiconductor equipment which is used to perform a specific manufacturing process over semiconductor silicon wafers without changing the optic sensor or the whole machine.

In a preferred embodiment, the present invention provides a method of detecting a transparent quartz wafer in a semiconductor equipment comprising a light source and an optic sensor for detecting the light transmitted from the light source, wherein when the semiconductor silicon wafer is moved to a predetermined position in the semiconductor equipment, the semiconductor silicon wafer will block the light transmitted from the light source to the optic sensor and then the semiconductor equipment will be switched on to perform the specific manufacturing process when the optic detector detects that the light from the light source is blocked; the method comprising:

forming at least one thin film layer at a bottom side of the quartz wafer over which the thin film layer can absorb at least portion of light transmitted from the light source; and moving the quartz wafer to the predetermined position in the semiconductor wherein the thin film layer at the bottom side of the quartz wafer will absorb the light transmitted from the light source to the optic sensor so as to make the optic sensor to detect the existence of the quartz wafer and then the semiconductor equipment will be switched on to perform the specific manufacturing process when the optic detector detects that the light from the light source is blocked.

It is an advantage of the present invention that the semiconductor equipment can be used to perform the manufacturing process over quartz wafers without changing its optic sensor. Therefore, the processing cost for the quartz wafer can be reduced, and the application of the semiconductor equipment becomes broader because the semiconductor equipment can be used in both semiconductor silicon wafers and the quartz wafers.

These and other objectives of the present invention will no doubt become obvious to those of ordinary skill in the art after reading the following detailed description of the preferred embodiment which is illustrated in the various figures and drawings.

DETAILED DESCRIPTION OF THE PREFERRED EMBODIMENT

Figure 1:
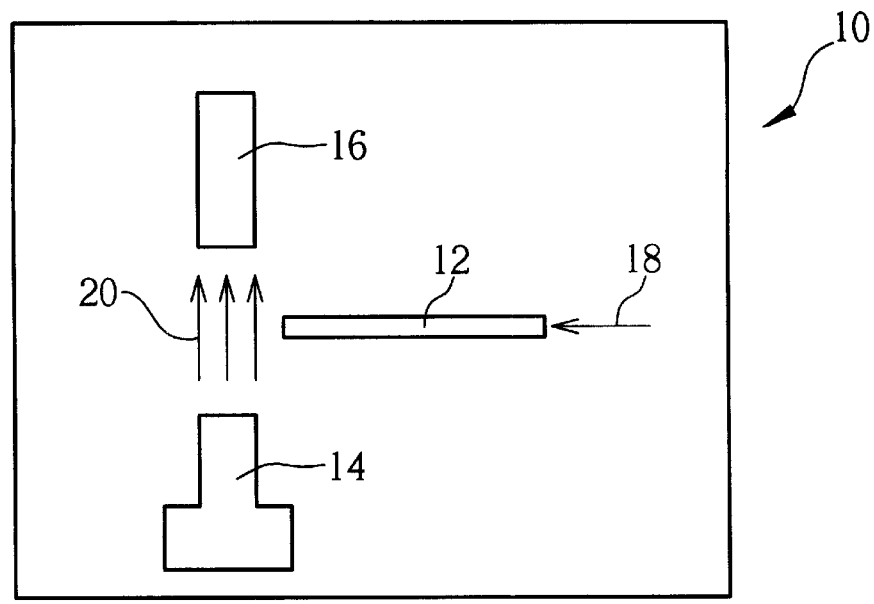
FIG. 1 is a schematic diagram of a method of detecting a silicon wafer in a semiconductor equipment according to the prior art.
Figure 2:
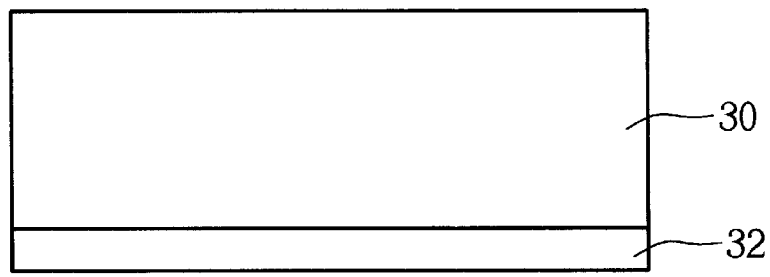
FIG. 2 is a schematic diagram of a method of detecting a quartz wafer in a semiconductor equipment according to the present invention.

Please refer to FIG. 2. FIG. 2 is schematic diagram of the method of detecting the quartz wafer in the semiconductor equipment according to the present invention. The present invention provides a method of detecting a transparent quartz wafer 30 in a semiconductor equipment 10. The semiconductor equipment 10 is used to perform a specific manufacturing process over a semiconductor silicon wafer, and comprises a light source 14 and a optic sensor 16, as shown in FIG. 1. The light source 14 is a red light or an infrared source, the optic sensor 16 is used to detect the light 20 transmitted from the light source 14. When the semiconductor silicon wafer 12 is moved to a predetermined position in the semiconductor equipment 10, the semiconductor silicon wafer 12 will block the light 20 transmitted from the light source 14 to the optic sensor 16 and then the semiconductor equipment 10 will be switched on to perform the specific manufacturing process.

The method in the present invention comprises forming a thin film layer 32 at the bottom side of the quartz wafer 30 over which the thin film layer can absorb at least portion of light transmitted from the light source 14, and moving the quartz wafer 30 to the predetermined position in the semiconductor equipment 10. As the quartz wafer 30 is moved to the predetermined position in the semiconductor equipment 10, the thin film layer 32 at the bottom side of the quartz wafer 30 will absorb at least portion light transmitted from light source 14 to optic sensor 16, so as to make the optic sensor 16 to detect the existence of the quartz wafer 30. And then the semiconductor equipment 10 will be switched on to perform the specific manufacturing process when the optic sensor 16 detects that the light from the light source 14 is blocked.

The thin film layer 32 is formed of a material with good absorption intensity of light, such as polysilicon commonly used in semiconductor manufacturing processes. Because the thin film layer 32 will absorb the energy of portion of light transmitted from the light source 14, the optic sensor 16 can ascertain that the quartz wafer 30 has reached the predetermined position by detecting changes in the energy of light intensity, and hence the semiconductor equipment can be switched on to perform the specific manufacturing process. Because of the thin film layer 32 at the bottom side of the quartz wafer 30, the semiconductor equipment 10 which is used to detect the semiconductor silicon wafer can also detect the quartz wafer 30. Therefore, the semiconductor equipment 10 can be used to perform the specific manufacturing process over the quartz wafer 30 without replacing its optic sensor 16 with other sensor particularly used for detecting the quartz wafer 30. After finishing the specific manufacturing process or the subsequent processes, the thin film layer 32 may be removed depending on the requirement for the absorption of the quartz wafer 30.

Figure 3:
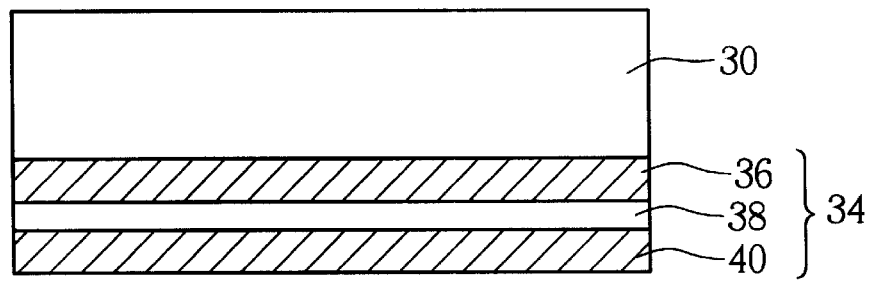
FIG. 3 is a schematic diagram of a quartz wafer of an alternative method according to the present invention.

Please refer to FIG. 3. FIG. 3 is a schematic diagram of a quartz wafer 30 in an alternative method according to the present invention. The alternative method according to the present invention is to form a thin film layer 34 at the bottom side of the quartz wafer 30 wherein the thin film layer 34 is formed by depositing a plurality of medium layers with different refraction indices respectively. Because light is a form of electromagnetic wave, the electromagnetic wave will reflect and refract in parts when passing through the interface of different mediums. When the light 20 passes through each of the interfaces of the thin film layer 34, it will reflect and refract for many times, resulting in the decrease in the light penetrating rate. Therefore, the optic sensor 16 can detect the existence of the quartz wafer 30 as the quartz wafer 30 reaches the predetermined position.

The thin film layer 34 in this method of the present invention comprises three medium layers with different refraction indices respectively. When forming the thin film layer 34, at first a poly-silicon layer 36 is formed at the bottom side of the quartz wafer 30, and then a silicon oxide layer 38 is formed at the bottom of the first poly-silicon layer 36, and at last a second poly-silicon layer 40 is formed at the bottom of the silicon oxide layer 38. Because these mediums are materials commonly used in semiconductor manufacturing processes at present, the thin film layer 34 can be formed conveniently. Using a common optic sensor which can detect the light in the range of visible light wavelengths to detect the thin film layer 34, the light penetrating rate through the thin film layer 34 is decreased from 100% to 40%. Therefore, the common optic sensor can detect the existence of the quartz wafer 30.

The method of the present invention is characterized in forming at least one thin film layer at the bottom side of the quartz wafer over which the thin film layer can absorb at least portion of light transmitted from the light source, or forming a thin film formed by a plurality of medium layers with different refraction indices to decrease the light penetrating rate through the quartz wafer, so as to make the optic sensor to detect the existence of the quartz wafer while the quartz wafer has reached the predetermined position in the semiconductor equipment. Therefore, the semiconductor equipment can be used to perform the manufacturing process without changing its original optic sensor, and hence the processing cost for the quartz wafer can be reduced. As the semiconductor equipment can be used to perform the manufacturing process over both semiconductor silicon wafers and the quartz wafers, the application of the semiconductor equipment becomes broader.

In contrast to the prior art method of detecting a quartz wafer in a semiconductor equipment in which the optic sensor cannot detect the quartz wafers, the method of the present invention can solve the problem in the prior art method. This invention method is forming a thin film layer 32 at the bottom side of the quartz wafer 30 over which the thin film layer 32 can absorb at least portion of light transmitted from the light source 14, so as to make the optic sensor to detect the existence of the quartz wafer as the quartz wafer reaches the predetermined position. Therefore, the semiconductor equipment can be used to perform the specific manufacturing process over the quartz wafers without changing its optic sensor.

Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of detecting a transparent quartz wafer in a semiconductor equipment, the semiconductor equipment being used to perform a specific manufacturing process over semiconductor silicon wafers and comprising a light source and an optic sensor for detecting the light transmitted from the light source, wherein when the semiconductor silicon wafer is moved to a predetermined position in the semiconductor equipment, the semiconductor silicon wafer will block the light transmitted from the light source to the optic sensor and then the semiconductor equipment will be switched on to perform the specific manufacturing process when the optic detector detects that the light from the light source is blocked; the method comprising:

forming at least one thin film layer at a bottom side of a quartz wafer over which the thin film layer can absorb at least a portion of the light transmitted from the light source; and moving the quartz wafer to the predetermined position in the semiconductor equipment wherein the thin film layer at the bottom side of the quartz wafer will absorb the light transmitted from the light source to the optic sensor so as to make the optic sensor to detect the existence of the quartz wafer and then the semiconductor equipment will be switched on to perform the specific manufacturing process.

2. The method of claim 1 wherein the thin film layer is formed of polysilicon.

3. The method of claim 1 wherein the thin film layer is formed by a plurality of medium layers with different refraction indices respectively.

4. The method of claim 3 wherein the plurality of medium layers comprises a polysilicon layer formed on the bottom side of the quartz wafer, a silicon oxide layer formed on the polysilicon layer, and another polysilicon layer formed on the silicon oxide layer.

5. The method of claim 1 wherein the light source is an infrared or a red light source.

\* \* \* \* \*